US006629321B1

(12) United States Patent
Hunt et al.

(10) Patent No.: US 6,629,321 B1
(45) Date of Patent: Oct. 7, 2003

(54) APPARATUS FOR AND METHOD OF DISPLAYING AND TRANSPORTING HUMAN REMAINS

(75) Inventors: Scot B. Hunt, Waldron, IN (US); Dale Meyer, Batesville, IN (US)

(73) Assignee: Batesville Services, Inc., Batesville, IN (US)

( * ) Notice: Subject to any disclaimer, the term of this patent is extended or adjusted under 35 U.S.C. 154(b) by 1397 days.

(21) Appl. No.: 08/627,089

(22) Filed: Apr. 3, 1996

(51) Int. Cl.[7] .......... A61B 17/00

(52) U.S. Cl. .......... 5/2.1; 5/3; 5/907; 27/27; 27/35; 108/157

(58) Field of Search .......... 5/94, 400, 411, 5/625, 627, 655, 907, 21, 3, 7, 12.1; 27/27, 28, 2, 4, 9, 14, 35; 108/153, 157, 159, 49

(56) References Cited

U.S. PATENT DOCUMENTS

| | | | | | |
|---|---|---|---|---|---|
| 235,376 | A | | 12/1880 | Orr | |
| 256,565 | A | * | 4/1882 | Hedenberg | 27/4 |
| 275,665 | A | | 4/1883 | Johnson | |
| 321,781 | A | | 7/1885 | Barrett | |
| 352,915 | A | | 11/1886 | Firnstein | |
| 559,457 | A | * | 5/1896 | Lautner | 27/4 |
| 737,580 | A | | 9/1903 | Carpenter | |
| 937,086 | A | | 10/1909 | Montross | |
| 1,292,268 | A | | 1/1919 | DeCamp | |
| 1,468,111 | A | | 9/1923 | Jones | |
| 1,497,597 | A | | 6/1924 | Scruggs | |
| 1,614,909 | A | | 1/1927 | Wolfram | |
| 1,824,156 | A | * | 9/1931 | Kimble | 5/12.1 |
| 2,033,807 | A | | 3/1936 | Baloga | |
| 2,050,675 | A | | 8/1936 | Tanner | |
| 2,198,997 | A | | 4/1940 | Hickey | |
| 2,359,193 | A | * | 9/1944 | Bechik | 5/703 |
| 2,532,355 | A | * | 12/1950 | Brown | 5/2.1 |
| 2,747,202 | A | * | 5/1956 | Driver | 5/2.1 |
| 2,759,239 | A | | 8/1956 | Snyder | |
| 2,802,253 | A | | 8/1957 | Birck | |
| 2,857,227 | A | * | 10/1958 | Jacques | 108/157 |
| 3,082,435 | A | * | 3/1963 | Philips et al. | 5/3 |
| 3,218,067 | A | * | 11/1965 | Beverly | 5/12.1 |
| 3,491,705 | A | * | 1/1970 | Blanke | 108/49 |
| D218,890 | S | | 10/1970 | Kreminski | |
| 3,581,318 | A | * | 6/1971 | Kroupa | 5/2.1 |
| 3,613,189 | A | | 10/1971 | Kirby | |
| 3,614,156 | A | | 10/1971 | Sarvas | |
| 3,732,583 | A | * | 5/1973 | Jones | 5/3 |
| 4,017,947 | A | | 4/1977 | Acton | |
| 4,063,337 | A | * | 12/1977 | Havey, III | 27/2 |
| 4,064,574 | A | | 12/1977 | Schnitzler | |
| 4,123,831 | A | | 11/1978 | Covington | |
| 4,176,431 | A | | 12/1979 | Havey, III | |
| 4,216,933 | A | | 8/1980 | Cramer | |

(List continued on next page.)

*Primary Examiner*—Robert G. Santos
(74) *Attorney, Agent, or Firm*—Wood, Herron & Evans, L.L.P.

(57) ABSTRACT

A support structure is configured into the appearance of a day bed. A body supporting and transporting tray is removably positioned atop the support structure and comprises a bottom, a pair of opposed sides and a pair of opposed ends. Each end includes a pair of elongated horizontal slots therein serving as handholds for grasping and lifting the tray. The support structure comprises a rectangular, planar platform having opposed front and rear edges and opposed end edges. Legs are connected to the platform and extend downwardly to support the platform above a floor surface. A back is connected to the rear edge of the platform along a lower edge of the back, the back projecting upwardly from the platform. A side is connected to each end edge of the platform and to a respective side edge of the back, with each side projecting upwardly from the platform. The support structure is convertible into a memorial table by substituting a table top structure for the tray.

56 Claims, 2 Drawing Sheets

U.S. PATENT DOCUMENTS

| | | | | |
|---|---|---|---|---|
| 4,315,354 | A | | 2/1982 | Behrendt |
| 4,372,018 | A | | 2/1983 | Miller, IV et al. |
| 4,569,095 | A | | 2/1986 | Holling |
| 4,829,639 | A | | 5/1989 | Woedl et al. |
| 5,282,439 | A | | 2/1994 | Oaks |
| 5,353,484 | A | | 10/1994 | Woedl et al. |
| 5,404,627 | A | * | 4/1995 | Shepherd ......................... 27/2 |
| 5,454,141 | A | | 10/1995 | Ozbun et al. |
| 5,586,376 | A | | 12/1996 | Enneking et al. |

* cited by examiner

APPARATUS FOR AND METHOD OF DISPLAYING AND TRANSPORTING HUMAN REMAINS

FIELD OF THE INVENTION

This invention relates generally to undertaking, and more particularly to apparatus for and method of displaying human remains for viewing purposes, for example at a memorial service or the like, and subsequently transporting those remains to a final destination for ultimate disposition, for example to a crematory for cremation.

BACKGROUND OF THE INVENTION

Traditionally, the body of a deceased has been presented in a casket selected by surviving members of the deceased's family for display of the body for viewing by mourners at a funeral or other memorial service. Subsequently, if in-ground burial was chosen by the surviving family members, the body would be buried in the selected casket.

Some find it distressing or otherwise objectionable to view their deceased loved one in a casket at the funeral or other memorial service. One attempt to remedy this problem is disclosed in Tanner U.S. Pat. No. 2,050,675. In Tanner there is disclosed a casket which converts from a casket to a couch or sofa and back again to a casket. To convert the casket to a couch, the casket lid is removed and a couch back and couch arms are removably mounted to the back and end edges of the casket shell. An upper portion of the casket shell front wall pivots downwardly and upholstery overlays and hides the downwardly pivoted portion. Pillows are added to the "couch" to enhance its couch-like appearance. A body may then be displayed on this "couch" providing a more natural, serene and less distressing appearance than that achievable when displaying the body in a casket. After viewing and prior to burial, the couch arms and back are removed from the casket shell (for subsequent reuse), the forward shell portion is pivoted upwardly and the lid is replaced to return the casket to its original configuration for burial purposes.

Other more conventional supports or furniture items, in addition to couches or sofas, which have heretofore been utilized to display bodies supported thereby for viewing thereof include beds and day beds, a day bed being a structure which includes a conventional bed mattress supported on a frame having a couch-like "back" and "arms". When "made up" a day bed appears much like a couch and is usable as such, but when "turned down" at night is utilizable as a bed. The couch "back" may be designed to resemble a bed headboard.

Cremation is a growing segment of the undertaking industry. While initially such services as embalming and funeral or memorial services were likely not desired by the surviving family members of the deceased when cremation was chosen as the method of ultimate disposition of the remains of the deceased (known as "direct cremation"), a growing portion of cremation customers are requesting of funeral directors and funeral homes that such traditional services be provided in addition to the service of cremation.

Cremation presents its own peculiar problems associated with dignified handling of the body up to and including the time the body is cremated. A cremation casket, generally a traditional appearing wooden casket with little or no metal used in its construction, and including the traditional casket interior trimmings, is one alternative for dignified handling of the body and display of the body if embalming and funeral or memorial services are requested. Such cremation caskets can be relatively expensive, however, and some object to burning such a casket with the body during cremation. Some of the cost can be eliminated by substituting less expensive materials, such as fiberboard (sometimes known as "hardboard"), for the more costly wood, though, as can be expected, there will be a consequent reduction in the aesthetics of the appearance of the product, which can be proportionate to the cost savings.

Another cremation alternative is a so-called cremation container, generally fabricated of cardboard and including no decorative interior. Such containers are much less expensive than cremation caskets and as such it is generally not objectionable to burn the container during cremation of the body. However, as can be expected, such containers are not particularly suited for display of a body for viewing or for a funeral or other memorial service do to their inexpensive construction and consequent sparse appearance.

One proposed solution to the problem of providing an attractive casket for viewing purposes without requiring a customer to purchase the casket and burn it during cremation is the so-called rental casket. Such caskets are generally fabricated of the same quality of materials and workmanship as traditional burial caskets, but may include certain specialized features such as a pivoting shell end wall which allows a body, contained in a cardboard box for instance, to be slid into and out of the casket from the end. In this way, a customer need only rent the use of the attractive, traditional casket for the viewing or the funeral service while purchasing only the cardboard box for handling and transportation of the body to the crematory. One example of such a casket is disclosed in Kirby U.S. Pat. No. 3,613,189.

A similar proposed solution is the use of a permanent casket "facade" which is removably placed over a disposable bottom container which includes bedding therein. The facade, placed over the container bottom, gives the appearance of a conventional casket. When the deceased is to be cremated, the facade is removed and the container bottom and the bedding within it, together with the deceased are covered with a cover member and sent to the crematory. The removable casket shell is thus not destroyed and can be reused during another funeral ceremony. Examples of such are disclosed in Havey, III U.S. Pat. Nos. 4,063,337 and 4,176,431.

However, these proposed solutions, while eliminating the necessity of burning a relatively expensive casket during the cremation, nonetheless suffer from the disadvantage mentioned above associated with the display of a body in any casket, namely, that many find the display of a deceased loved one in a casket especially distressing in their time of grief.

It is therefore a main objective of the present invention to provide apparatus for and method of displaying human remains for viewing purposes and for transporting the remains to a final destination for ultimate disposition, yet which do not result in the destruction of a relatively expensive casket, by way of either in-ground burial or cremation, and which do not compound the distress experienced by grieving loved ones by having to view the loved ones' deceased being displayed in a traditional casket.

SUMMARY OF THE INVENTION

In accordance with the stated objective, the present invention provides both apparatus for and method of displaying human remains for viewing purposes and for transporting the remains to a final destination for ultimate disposition, yet which do not suffer from the many disadvantages of the prior art products and techniques. The apparatus of the present invention comprises a support structure configured into the appearance of a day bed and adapted to support and display the body of a deceased. A body supporting and transporting tray is removably positioned atop the support structure. The tray supports a body thereon when positioned atop the support structure and, when removed from the support structure, transports the body to a final destination for ultimate disposition.

The body supporting tray of the present invention comprises a bottom, a pair of opposed sides connected to the bottom and a pair of opposed ends connected to the bottom and to the pair of sides. Each end of the pair of ends includes a pair of elongated horizontal slots therein serving as handholds for grasping and lifting the tray.

The support structure preferably includes a back with an upper edge having a decorative profile. At least one of the tray sides includes an upper edge which has a decorative profile which complements the decorative profile of the upper edge of the back. The support structure is preferably open and unobstructed along a forward edge such that the tray side upper edge decorative profile is visible from the front of the support structure when the tray is positioned atop the support structure.

When cremation is chosen as the means of ultimate disposition of the remains, the tray is fabricated of a combustible material such that the tray may be cremated along with the body.

The support structure may be preferably constructed of decorative wood normally associated with fine furniture, such as cherry. The tray may be preferably fabricated of a lesser expensive wood, such as poplar or maple, but which can be finished to closely match the cherry wood of the support structure.

A mattress is provided for placement into the bottom of the tray. While most any type of decorative bedding can be used atop the mattress to display a body supported on the tray and the support structure, one particular type of bedding which is most attractive on the tray and support structure is a quilt. A matching pillow covered with the same type of fabric as makes up the quilt is also preferably provided to complete the display.

In a preferred form, the day bed configured support structure comprises a rectangular, planar platform having opposed front and rear edges and opposed end edges. Legs are connected to the platform and extend downwardly from the platform to support the platform above a floor surface. A back is connected to the rear edge of the platform along a lower edge of the back, the back projecting upwardly from the platform. A side is connected to each end edge of the platform and to a respective side edge of the back, with each side projecting upwardly from the platform. A cover plate is preferably included at either end of the support structure and is removably placed atop the legs. The cover plates, when removed, permit easier placement of the tray onto the support structure and removal of the tray from the support structure. When installed, the cover plates provide a smooth, clean, finished appearance of the support structure with tray thereon.

The support structure and tray are preferably constructed so as to position a deceased approximately 30 inches above a supporting floor surface. The support structure is preferably approximately 94 inches long and approximately 30 inches wide. The tray is preferably approximately 83 inches long and approximately 28 inches wide.

In its broadest aspect, the method of the present comprises the steps of providing a support structure configured into the appearance of a day bed and adapted to support and display the body of a deceased, providing a body supporting and transporting tray, positioning a body on the tray, removably positioning the tray on the support structure, displaying the body on the tray and support structure to those wishing to view the body and subsequently transporting the body on the tray to a final destination for ultimate disposition thereof. It is contemplated that the final destination of the body and tray is a crematory and that the ultimate disposition of the body and the tray is by cremation in the preferred form of carrying out the method of the present invention. The method may further comprise the steps of providing a table top structure, positioning the table top structure on the support structure and displaying an urn containing the cremated remains of the body therein on the table top structure.

In another aspect of the present invention, apparatus for displaying human remains for viewing purposes and for transporting the remains to a final destination for ultimate disposition, which apparatus is convertible into a memorial table, is provided. The apparatus comprises a support structure configured into the appearance of a day bed and adapted to support and display the body of a deceased. A body supporting and transporting tray is adapted to be removably positioned atop the support structure. A table top structure is also adapted to be removably positioned atop the support structure in the absence of the tray. The table top structure is for supporting and displaying an urn containing cremated remains, pictures, flowers, mementos and the like. The support structure is thus usable serially as a body supporting daybed-like rest bed and as a memorial table.

The present invention has numerous advantages. A technique of displaying a body for viewing and funeral or other memorial type service is provided which does not require the body to be displayed in a traditional casket, which compounds the grief of loved ones. The body is presented in a much more natural and serene manner. The support structure provided by the present invention appears to be an attractively designed day bed. The tray of the present invention which cooperates with the support structure is designed to complement the day bed configured support structure. A quilt is provided for covering the body on the tray and support structure, which complements the finished wood of the support structure and tray. The appearance of the deceased on the apparatus of the present invention engenders a memorial image of the deceased resting peacefully on an attractive piece of furniture—a day bed.

The tray may then readily be used to transport the deceased to a crematory. The tray may itself be cremated along with the body without a great investment loss since it can be economically manufactured. The support structure may then be reused. Customers are not required to purchase a relatively expensive casket to obtain an elegant look for viewing and the funeral or to destroy such a casket in a crematory; customers need only rent the use of the support structure which is less expensive than a relatively expensive casket.

The support structure is also readily converted into a memorial table by substituting the table top for the tray. The memorial table may be used subsequently to the tray and may display an urn containing the cremated remains of the deceased therein as a focal point of a memorial service or other ceremony. Or the memorial table may be used to display simply pictures, flowers and other mementos and the like of the deceased, and is thus usable whether cremation or conventional in-ground or above-ground burial is chosen.

These and other objects and advantages of the present invention will become more readily apparent during the following detailed description taken in conjunction with the drawings herein, in which:

DETAILED DESCRIPTION OF THE INVENTION

Figure 1:
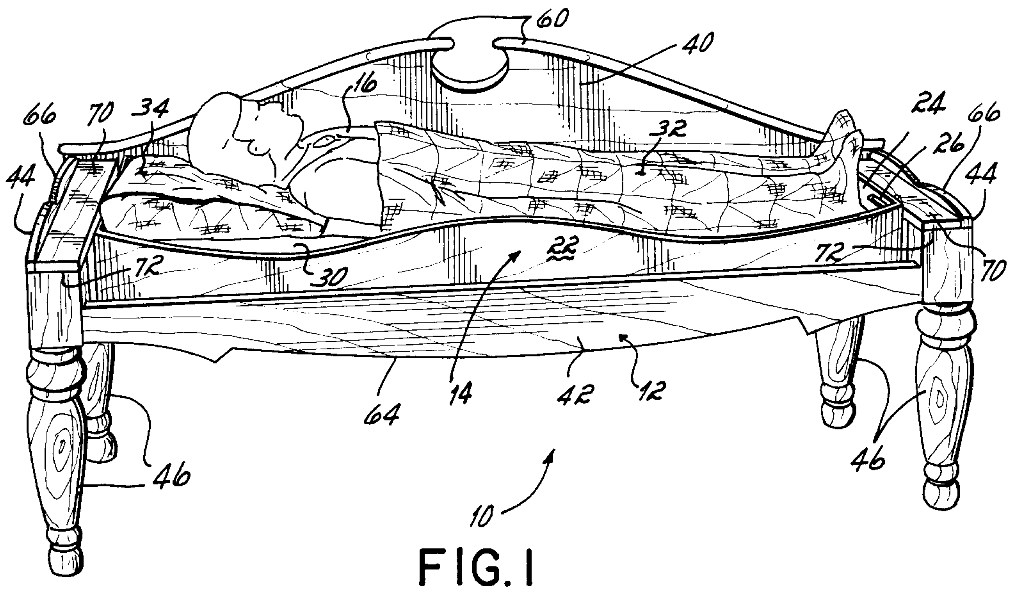
FIG. 1 is a front perspective view of the apparatus of the present invention.

Referring first to FIG. 1, there is illustrated apparatus 10 according to the principles of the present invention. The apparatus 10 is for displaying human remains for viewing purposes and for transporting the remains to a final destination for ultimate disposition, as will be more fully described below.

The apparatus 10 comprises, generally, a support structure 12, and a body supporting and transporting tray 14. The support structure 12 is configured generally into the appearance of a day bed, though as will be described subsequently in more detail, the support structure 12 is particularly constructed and arranged, or adapted, to support and display the body of a deceased. The tray 14 is removably positionable on the support structure 12. The tray 14 is for supporting a body 16 thereon when positioned atop the support structure 12, and, when removed from the support structure 12, for transporting the body to a final destination for ultimate disposition.

Figure 2:
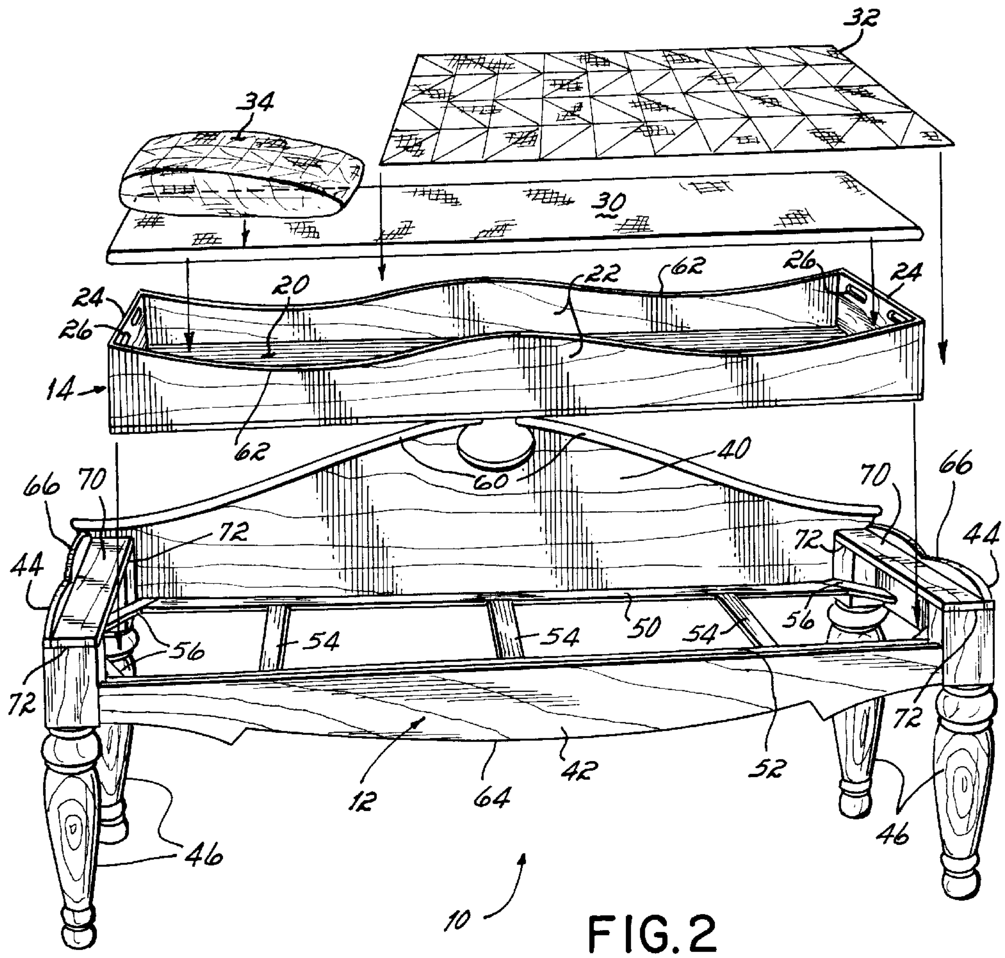
FIG. 2 is a front perspective view, exploded, of the apparatus of FIG. 1.

Referring now to FIGS. 1 and 2, tray 14 includes a bottom 20, a pair of opposed sides 22 connected to the bottom 20, and a pair of opposed ends 24 connected to the bottom 20 and to the pair of sides 22. Each end 24 of the tray 14 includes a pair of elongated horizontal slots 26 therein which serve as hand holds for grasping and lifting the tray. The tray 14 is preferably fabricated of a combustible material such that the tray may be cremated along with the body 16 at the final destination, for example crematory. The tray 14 is preferably fabricated of wood such as poplar or maple, which may be attractively finished to match the wood of the support structure 12, but yet which is less expensive than the wood utilized in the support structure 12.

A mattress 30 is provided for positioning atop the bottom 20 of the tray 14. The mattress 30 is approximately three inches thick. Decorative bedding, for example, quilt 32, is provided for covering the body 16 atop the mattress 30. Further, a matching pillow 34 is also provided which preferably matches the bedding 32. The tray 14 is approximately 83 inches long by 28 inches wide.

The support structure 12 is preferably fabricated of fine wood such as that found in fine furniture, for example of cherry. The structure 12, as discussed above, is generally configured into the appearance of a day bed. The structure 12 includes a back 40, a front 42 and opposed ends 44. Four legs 46 are provided at the four corners of the structure 12 for supporting it above a floor surface. The back 40, front 42, ends 44 and legs 46 are preferably secured together as by screws (not shown) or the like. A cleat 50 is secured to the back 40 along its lower edge as by screws (not shown). A similar cleat 52 is attached to the upper edge of the front 42. A number of transverse slats 54 are attached to the cleats. Corner braces 56 are secured to the legs 46, back 40, sides 44 and front 42, and the cleats 50, 52, also with the use of screws (not shown). The structure 12 thus provides a generally rectangular, planar platform atop which the tray 14 may be supported. By constructing the support 12 with an "open" supporting platform via the cleats 50, 52 and slats 54 (i.e. as opposed to including a continuous solid wood platform), the costs associated with manufacturing the support 12 are reduced.

As shown in the drawings, the support structure 12 includes a number of decorative features which enhance its appearance and present the appearance of an attractive, elegant day bed. The back 40 is generally in the shape of a "headboard" and includes a decorative upper edge 60. The sides 22 of a tray 14 also include decorative upper edges 62 which generally compliment the decorative upper edge 60 of the back 40. The front 42 includes a decorative lower edge 64. As the tray 14 generally rests atop the top edge of the front 42, the support structure 12 is generally open and unobstructed at its forward edge at the level of the supporting platform portion of the support structure such that the forward side 22 of the tray 14 is visible. The sides 44 include decorative upper edges 66 which similarly enhance and compliment the decorative edges of the back 40, front 42 and tray sides 22. Legs 46 are attractively of turned construction. Cover plates 70 may be placed atop the tops 72 of the posts 46 to present a smooth, clean finished appearance for the structure 12 with the tray supported thereon (FIG. 1), but may also be removed to facilitate placement and removal of tray 14 onto and from the structure 12. When cover plates 70 are removed, the space between the tops 72 of posts 46 becomes available to accommodate a person's hands which grasp the tray 14 via handholds 26, thus preventing skinning of knuckles, etc. Once the tray 14 is installed onto the support 12, the plates 70 may be replaced atop the posts 46 as described. Plates 70 may be hinged to the structure 12 to prevent inadvertinent dropping or loss thereof.

The cleats 50, 52, slats 54 and corner reinforcers 56 preferably position the bottom 20 of the tray 14 at a height of approximately 25½ inches above a supporting floor surface. The tray 14 is preferably fabricated such that the upper surface of the bottom 20 of the tray 14 is approximately 1¾ inches from the lower surface of the bottom 20 of the tray 14, i.e. the surface which contacts the support structure 12. With a three inch mattress 30 installed therein, the deceased 16 is thus positioned approximately 30 inches above a supporting floor surface. The overall length and width of the support structure 12 is approximately 94 inches long by 30 inches wide, with a five inch square dimension of the upper ends 72 of the posts 46 providing approximately 84 inches allowable length for the tray 14 which is preferably approximately 83 inches long by 28 inches wide. Thus, while being configured generally as a day bed, the support structure 12 as described herein is nevertheless specially adapted to support and display the body of a deceased, having a body supporting surface higher and narrower than that of a day bed.

In use, the support structure 12 is positioned in the funeral home viewing area or the like, the body 16 is prepared and positioned on the tray 14, and the tray 14 is placed upon the support structure 12. The lower portion of the body 16 is covered with bedding 32 as described above. A traditional viewing of the body 16 may then be had. Thereafter, the hand holds 26 of the tray 14 are grasped by pall bearers or funeral home aids and the body 16 is transported via the tray to its final destination for ultimate disposition. When cremation has been chosen, the tray 14, fabricated relatively inexpensively, may be combusted along with the body 16. The support 12 may then be reused. However, it will be appreciated that the present invention is not limited solely to cremation, as the tray 14 could be utilized to transport the body 16 to, for example, a gravesite or the like, in which case both the tray 14 and the support structure 12 would be reused.

Figure 3:
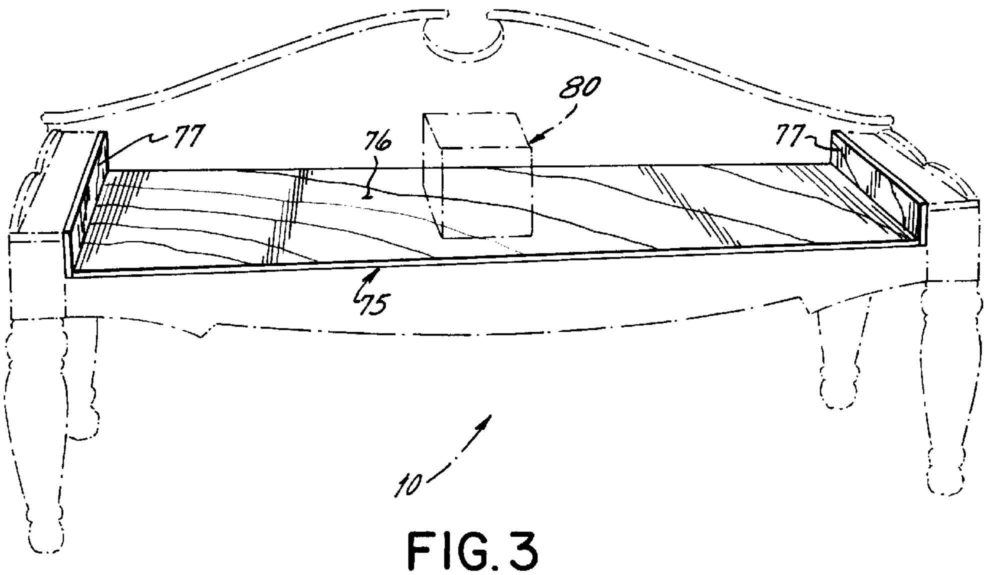
FIG. 3 is a front perspective view of the apparatus of the present invention transformed into a memorial table.

Referring now to FIG. 3, another use of the structure 12 is illustrated. In this embodiment, a table top structure 75 is placed atop the support 12 (phantom) and the combination serves as a "memorial table". The table top structure 75 comprises a table top portion 76 with an upstanding end portion 77 extending upwardly from each end thereof. Ends 77 provide a clean appearance for the memorial table, concealing the sides of the legs 46 and the open space therebetween. Table top structure 75 is preferably fabricated of the same attractive wood as that of the support structure 12. Alternatively, table top structure 75 could be fabricated out of other attractive materials, for example marble.

An urn 80 (phantom) containing the ashes of the deceased may be placed on the memorial table of FIG. 3 as a focal point for a memorial service or the like for the deceased. Flowers, pictures and other mementos may be placed around the urn 80. Alternatively, only the flowers, pictures, mementos and the like can be placed on the memorial table if it is not desired to display the urn thereon. The memorial table may be also utilized in conventional casket ceremonies or services for the placement thereon of flowers, pictures or the like.

Thus, the structure 12 serves the dual functions of providing an attractive, serene supporting structure for a deceased, i.e. a "rest bed", as well as providing a memorial table for the deceased. In this way the invention provides a "memorial rest system" which funeral directors may utilize for cremation or traditional in-ground or above-ground burial, for viewing, funeral services, memorial services or other ceremonies as the need arises.

Those skilled in the art will readily recognize numerous adaptations and modifications which can be made to the present invention which will result in an improved apparatus for and method of displaying human remains for viewing purposes and transporting the remains to a final destination for ultimate disposition, yet all of which will fall within the spirit and scope of the present invention as defined in the following claims. Accordingly, the invention is to be limited only by the scope of the following claims and their equivalents.

What is claimed is:

1. Apparatus for displaying human remains for viewing purposes and for transporting the remains to a final destination for ultimate disposition, said apparatus comprising in combination:

a support structure configured into the appearance of a day bed and adapted to support and display the body of a deceased; and a body supporting and transporting tray removably positioned atop said support structure, said tray for supporting a body thereon when positioned atop said support structure and, when removed from said support structure, for transporting the body to a final destination for ultimate disposition thereof.

2. The combination of claim 1 wherein said tray comprises:

a bottom;

a pair of opposed sides connected to said bottom; and a pair of opposed ends connected to said bottom and to said pair of sides, each end of said pair of ends including a pair of elongated horizontal slots therein serving as handholds for grasping and lifting said tray.

3. The combination of claim 2 wherein said support structure includes a back with an upper edge having a decorative profile and wherein at least one of said tray sides includes an upper edge having a decorative profile which complements said decorative profile of said back upper edge.

4. The combination of claim 3 wherein said support structure is open and unobstructed along a forward edge thereof such that said at least one tray side including said upper edge decorative profile is visible from the front of said support structure when said tray is positioned atop said support structure.

5. The combination of claim 4 wherein said tray is fabricated of a combustible material such that said tray may be cremated along with the body at the final destination.

6. The combination of claim 5 wherein said support structure is constructed of cherry wood.

7. The combination of claim 6 wherein said tray is constructed of poplar or maple, and is finished to match said cherry wood of said support structure.

8. The combination of claim 7 wherein said tray includes a mattress positioned therein on said tray bottom.

9. The combination of claim 8 wherein said tray includes a quilt overlying said mattress, and a pillow which matches said quilt.

10. The combination of claim 1 wherein said support structure and tray position a deceased approximately 30 inches above a supporting floor surface.

11. The combination of claim 10 wherein said support structure is approximately 94 inches long and approximately 30 inches wide.

12. The combination of claim 11 wherein said try is approximately 83 inches long and approximately 28 inches wide.

13. Apparatus for displaying human remains for viewing purposes and for transporting the remains to a final destination for ultimate disposition, said apparatus comprising in combination:

a support structure configured into the appearance of a day bed and adapted to support and display the body of a deceased and comprising:

a rectangular, planar platform having opposed front and rear edges and opposed end edges;

legs connected to said platform and extending downwardly from said platform to support said platform above a floor surface;

a back connected to said rear edge of said platform along a lower edge of said back, said back projecting upwardly from said platform; and a side connected to each said end edge of said platform and to a respective side edge of said back, each said side projecting upwardly from said platform; and a body supporting and transporting tray removably positioned atop said platform, said tray for supporting a body thereon when positioned atop said platform and, when removed from said platform, for transporting the body to a final destination for ultimate disposition thereof.

14. The combination of claim 13 wherein said tray comprises:

a bottom;

a pair of opposed sides connected to said bottom; and a pair of opposed ends connected to said bottom and to said pair of sides, each end of said pair of ends including a pair of elongated horizontal slots therein serving as handholds for grasping and lifting said tray.

15. The combination of claim 14 wherein said support structure back includes an upper edge having a decorative profile and wherein at least one of said tray sides includes an upper edge having a decorative profile which complements said decorative profile of said back upper edge.

16. The combination of claim 15 wherein said support structure is open and unobstructed along a forward edge thereof at the level of said support platform such that said at least one tray side including said upper edge decorative profile is visible from the front of said support structure when said tray is positioned atop said platform.

17. The combination of claim 16 wherein said tray is fabricated of a combustible material such that said tray may be cremated along with the body at the final destination.

18. The combination of claim 17 wherein said support structure is constructed of cherry wood.

19. The combination of claim 18 wherein said tray is constructed of poplar or maple, and is finished to match said cherry wood of said support structure.

20. The combination of claim 19 wherein said tray includes a mattress positioned therein on said tray bottom.

21. The combination of claim 20 wherein said tray includes a quilt overlying said mattress, and a pillow which matches said quilt.

22. The combination of claim 13 wherein said support structure and tray position a deceased approximately 30 inches above a supporting floor surface.

23. The combination of claim 22 wherein said support structure is approximately 94 inches long and approximately 30 inches wide.

24. The combination of claim 23 wherein said tray is approximately 83 inches long and approximately 28 inches wide.

25. The combination of claim 13 further including a cover plate at either end of said support structure removably placed atop said legs, said cover plates, when removed, permitting easier placement of said tray onto said support structure and removal of said tray from said support structure, said cover plates, when installed, providing a smooth, clean, finished appearance of said support structure with said tray thereon.

26. A method of displaying human remains for viewing purposes and for transporting the remains to a final destination for ultimate disposition, the method comprising the steps of:

providing a support structure configured into the appearance of a day bed and adapted to support and display the body of a deceased;

providing a body supporting and transporting tray;

positioning a body on said tray;

removably positioning said tray on said support structure;

displaying the body on said tray and support structure to those wishing to view the body; and subsequently transporting the body on said tray to a final destination for ultimate disposition thereof.

27. The method of claim 26 wherein said support structure comprises:

a rectangular, planar platform having opposed front and rear edges and opposed end edges;

legs connected to said platform and extending downwardly from said platform to support said platform above a floor surface;

a back connected to said rear edge of said platform along a lower edge of said back, said back projecting upwardly from said platform; and a side connected to each said end edge of said platform and to a respective side edge of said back, each said side projecting upwardly from said platform.

28. The method of claim 27 wherein said tray comprises:

a bottom;

a pair of opposed sides connected to said bottom; and a pair of opposed ends connected to said bottom and to said pair of sides, each end of said pair of ends including a pair of elongated horizontal slots therein serving as handholds for grasping and lifting said tray.

29. The method of claim 28 wherein said support structure back includes an upper edge having a decorative profile and wherein at least one of said tray sides includes an upper edge having a decorative profile which complements said decorative profile of said back upper edge.

30. The method of claim 29 wherein said support structure is open and unobstructed along a forward edge thereof at the level of said support platform such that said at least one tray side including said upper edge decorative profile is visible from the front of said support structure when said tray is positioned atop said platform.

31. The method of claim 30 wherein said tray is fabricated of a combustible material such that said tray may be cremated along with the body at the final destination.

32. The method of claim 31 wherein said support structure is constructed of cherry wood.

33. The method of claim 32 wherein said tray is constructed of poplar or maple, and is finished to match said cherry wood of said support structure.

34. The method of claim 33 wherein said tray includes a mattress positioned therein on said tray bottom.

35. The method of claim 34 wherein said tray includes a quilt overlying said mattress, and a pillow which matches said quilt.

36. The method of claim 26 wherein the final destination of the body and said tray is a crematory and the ultimate disposition of the body and said tray is cremation.

37. The method of claim 26 further comprising the steps of:

providing a table top structure;

positioning said table top structure on said support structure; and displaying an urn containing the cremated remains of the body therein on said table top structure.

38. Apparatus for displaying human remains for viewing purposes and for transporting the remains to a final destination for ultimate disposition, said apparatus convertible into a memorial table, said apparatus comprising in combination:

a support structure configured into the appearance of a day bed and adapted to support and display the body of a deceased;

a body supporting and transporting tray adapted to be removably positioned atop said support structure, said tray for supporting a body thereon when positioned atop said support structure and, when removed from said support structure, for transporting the body to a final destination for ultimate disposition; and a table top structure adapted to be removably positioned atop said support structure in the absence of said tray, said table top structure for supporting cremated remains, pictures, mementos;

whereby said support structure is usable serially as a body supporting daybed-like rest bed and as a memorial table.

39. The combination of claim 38 wherein said support structure comprises:

a rectangular, planar platform having opposed front and rear edges and opposed end edges;

legs connected to said platform and extending downwardly from said platform to support said platform above a floor surface;

a back connected to said rear edge of said platform along a lower edge of said back, said back projecting upwardly from said platform; and a side connected to each said end edge of said platform and to a respective side edge of said back, each said side projecting upwardly from said platform.

40. The combination of claim 39 wherein said tray comprises:

a bottom;

a pair of opposed sides connected to said bottom; and a pair of opposed ends connected to said bottom and to said pair of sides, each end of said pair of ends including a pair of elongated horizontal slots therein serving as handholds for grasping and lifting said tray.

41. The combination of claim 40 wherein said table top structure comprises:

a table top portion having opposed ends; and an upstanding end portion extending upwardly from each said end of said table top portion.

42. An apparatus for displaying a body o a deceased, said apparatus being convertible into a memorial table for displaying cremated remains, pictures and mementos, said apparatus comprising:

a support structure;

a body-supporting tray resting on said support structure for carrying the body of the deceased when the body is displayed; and a table top resting on said support structure for carrying cremated remains, pictures and mementos, when the cremated remains, pictures and mementos are displayed.

43. The apparatus of claim 42, wherein said body-supporting tray is constructed in a structurally sufficient manner for transporting the body.

44. The apparatus of claim 42, wherein said body-supporting tray is made from crematable materials.

45. The apparatus of claim 42, wherein said support structure includes a generally rectangular, planar platform for carrying said body-supporting tray, said platform being carried by a plurality of legs engaging a floor, said legs having tops projecting above said platform.

46. The apparatus of claim 45, wherein said body-supporting tray includes a bottom and a pair of opposed ends, each said end being spaced longitudinally inwardly from respective adjacent legs of said support structure when said body-supporting tray rests on said platform.

47. The apparatus of claim 46, further comprising a plurality of cover plates, each said cover plate engaging the tops of at least two said legs, said cover plates and said body-supporting tray being positioned to lie so that each said end is adjacent a respective cover plate when said body-supporting tray rests on said support structure.

48. The apparatus of claim 46, wherein said tray ends project upwardly from a bottom of said tray and each said tray end is formed to include at least one generally horizontal slot for grasping and lifting said body-supporting tray.

49. The apparatus of claim 45, wherein said table top includes a generally planar portion resting on said platform when the cremated remains, pictures and mementos are displayed, said table top further having end portions extending generally upwardly from each end of said planar portion to the tops of said legs.

50. The apparatus of claim 49, wherein each said leg further includes a longitudinally inwardly-facing side extending from said platform to the top of said leg, and each end portion of said table top abuts said longitudinally inwardly-facing sides of respective ones of said legs.

51. The apparatus of claim 49, further comprising a plurality of cover plates, each said cover plate having a top surface and a bottom surface, said bottom surface of each said cover plate engaging the tops of at least two said legs, an upper edge of each said end portion being generally flush with the top surface of an adjacent said cover plate.

52. The apparatus of claim 45, wherein said support structure further includes a back extending generally upwardly from said platform, said back having an upper edge defining a decorative profile.

53. The apparatus of claim 52, wherein said body supporting tray includes a bottom and a pair of opposed ends, each said end being connected to said bottom and extending generally upwardly therefrom to an upper edge, said upper edge of each said end defining a decorative profile that complements said decorative profile of said back of said support structure.

54. The apparatus of claim 42, further comprising a mattress positioned to lie on said body-supporting tray beneath the body of the deceased.

55. The apparatus of claim 54, further comprising a quilt overlying said mattress and a pillow carried by said mattress, said pillow matching said quilt.

56. The apparatus of claim 42, wherein said support structure is open and unobstructed along a forward edge thereof so that said body-supporting tray can be easily moved onto and off of said support structure past said forward edge.

* * * * *

UNITED STATES PATENT AND TRADEMARK OFFICE

CERTIFICATE OF CORRECTION

PATENT NO. : 6,629,321 B1
APPLICATION NO. : 08/627089
DATED : October 7, 2003
INVENTOR(S) : Scot B. Hunt and Dale Meyer It is certified that error appears in the above-identified patent and that said Letters Patent is hereby corrected as shown below:

Column 6, line 40, “25 1/2” should be --25 1/4--.

Column 8, line 34, “try” should be --tray--.

Column 11, line 29, “a body o a deceased” should be --a body of a deceased--.

Signed and Sealed this

Twentieth Day of February, 2007

JON W. DUDAS
*Director of the United States Patent and Trademark Office*